United States Patent [19]

Truppe

[11] Patent Number: 5,678,546
[45] Date of Patent: Oct. 21, 1997

[54] METHOD FOR DISPLAYING MOVEABLE BODIES

[76] Inventor: Michael Truppe, Am Kanal 27, A-1110, Wien, Austria

[21] Appl. No.: 213,188

[22] Filed: Mar. 15, 1994

Related U.S. Application Data

[63] Continuation of Ser. No. 792,892, Nov. 15, 1991, abandoned.

[30] Foreign Application Priority Data

Nov. 26, 1990 [AT] Austria ................................ 2397/90
Nov. 26, 1990 [AT] Austria ................................ 2398/90

[51] Int. Cl.$^6$ ...................................................... A61B 5/05
[52] U.S. Cl. ...................... 128/653.1; 128/782; 128/898; 364/413.13
[58] Field of Search ............................ 128/660.04, 665, 128/782, 774, 898, 653.1, 660.1; 358/107; 378/4, 20, 21, 28, 29, 37, 62, 63, 98, 204, 210; 364/413.01, 413.02, 413.13, 413.14, 413.19, 413.21, 413.22, 413.25, 460; 356/1; 340/980

[56] References Cited

U.S. PATENT DOCUMENTS

| | | |
|---|---|---|
| 4,197,855 | 4/1980 | Lewin . |
| 4,550,984 | 11/1985 | Reymond . |
| 4,722,056 | 1/1988 | Roberts et al. . |
| 4,817,433 | 4/1989 | Sato . |
| 4,832,049 | 5/1989 | Matsushita et al. . |
| 4,922,909 | 5/1990 | Little et al. . |
| 4,930,888 | 6/1990 | Freisleben et al. . |
| 4,987,412 | 1/1991 | Vaitekunas et al. . |
| 5,007,428 | 4/1991 | Watmough . |
| 5,072,218 | 12/1991 | Spero et al. . |
| 5,099,846 | 3/1992 | Hardy . |
| 5,099,859 | 3/1992 | Bell . |
| 5,186,174 | 2/1993 | Schlondorff et al. . |

FOREIGN PATENT DOCUMENTS

| | | |
|---|---|---|
| 384544B | 11/1987 | Austria . |
| 0077193B1 | 4/1983 | European Pat. Off. . |
| 0119660A1 | 9/1984 | European Pat. Off. . |
| 0488987A1 | 6/1992 | European Pat. Off. . |
| 2545349A1 | 11/1984 | France . |
| 3406179C1 | 9/1985 | Germany . |
| 3532730A1 | 3/1987 | Germany . |
| 3807578A1 | 9/1989 | Germany . |
| 4134481A1 | 4/1993 | Germany . |

OTHER PUBLICATIONS

Maekawa et al., "Measurement of the Upper Limb Motion by a Magnetic Sensor and Its Application to Kinesiology Studies," pp. 1445–1445, IEEE Engineering in Medicine and Biology Society 11th Annual International Conference, 1989.

(List continued on next page.)

*Primary Examiner*—Guy V. Tucker
*Attorney, Agent, or Firm*—Broadbent, Hulse, Pierce & Pate

[57] ABSTRACT

The invention relates to a method for displaying moveable bodies, in which an optical representation of the body and a data field attributed to this body are displayed simultaneously or alternately from the same perspective and on the same scale in real time. The method includes the following steps:

providing the optical image-reproduction system comprising a camera and a monitor;

allocating a 3D - data field to the body having a certain position;

continuously recording of the 3D - position of the body;

continuously calculating of a display of the data field equivalent to the body's momentary position;

simultaneously or alternately representing the optical image and the data field on the monitor.

An apparatus for carrying out this method is also provided.

12 Claims, 1 Drawing Sheet

OTHER PUBLICATIONS

J. Gybels, D. Vandermeulen, P. Suetens, G. Marchal and G. Wilms, "A Prototype Medical Workstation for Computer-Assisted Stereotactic Neurosurgery." pp. 493–496, 10th meeting of the World Society for Stereotactic and Functional Neurosurgery, Maebashi, Japan, Oct. 1989.

P. Haigron and R. Collorec, "3D Surface Reconstruction Using Strongly Distorted Stereo Images," pp. 1050–1051, Annual International Conference of the IEEE Engineering in Medicine and Biology Society, vol. 13, No. 3, 1991.

Amami Kato, Toshiki Yoshimine and Hayakawa, "A Frameless, Armless Navigational System for Computer Assisted Neurosurgery." pp. 845–849, *J. Neurosurg*, vol. 74, May, 1991.

Michael Bajura, Henry Fuchs and Ryutarou Ohbuchi, "Merging Virtual Objects with the Real World: Seeing Ultrasound Imagery within the Patient." pp. 203–209, *Computer Graphics*, vol. 26.2, Jul., 1992.

Pavel Houdek, James Schwade, Christopher Serago, Howard Landy, Vincent Pisciotta, Xiaodong Wu, Arnold Markoe, Alan Lewin, Andre Abitbol, Joanne Bujnoski, Evelyn Marienberg, Jeffery Fiedler and Murray Ginsberg, "Computer Controlled Stereotaxic Radiotheraphy System." pp. 175–180, *Int. J. Radiation Oncology Biol. Phys.*, vol. 22, No. 1, 1992.

METHOD FOR DISPLAYING MOVEABLE BODIES

BACKGROUND

1. Related Applications

This application is a continuation of my application Ser. No. 07/792,892, filed on Nov. 15, 1991 for METHOD FOR DISPLAYING MOVEABLE BODIES, now abandoned.

2. The Field of the Invention

The invention relates to a method for displaying moveable bodies and, more particularly, to a method for displaying such bodies, which can move freely in a recording area, in real time.

3. The Background Art

It is often required in the fields of engineering and medicine to add information to the optical display of objects or to combine various displays of an object.

It is common and necessary, for example, to compare preoperative images with intraoperative images when carrying out certain operations on the human body. These images may concern two-dimensional X-rays, tomographies, ultrasonic images or nuclear spin tomographies.

In order to match two such images, it is now possible to identify a certain number of anatomically characteristic points and to determine the coordinates of said points in both images. Thereupon it is possible to calculate the six parameters of a solid-state body transformation, i.e. the three translatory and the three rotatory parameters and, optionally, a scaling factor. This allows rotating and displacing one of the two images in such a manner that both images can be displayed from same perspective and on the same scale. This process is called "matching".

The identification of the characteristic points by this method requires considerable effort and is susceptible to errors. In addition, it is possible to compare and display only two single images subsequently.

In order to simplify the matching it was proposed to attach certain markings on the object to be examined, whereby the markings are visible and easily identifiable in both images. These may be probes of suitable material whose positions on the X-rays can easily be determined. In the case of optical displays these probes may also consist of colored markings on the surface of the skin. However, this also only allows the subsequent representation of two single images.

In order to combine the optical display of an object with other displays, which can concern the above-mentioned two-dimensional X-rays, tomographies, ultrasonic images or nuclear spin tomographies or the like, it is principally possible to create at first a three-dimensional model of the surface of the body and then to save this model. This model can then be matched in the manner mentioned above with the data of a nuclear spin tomography. Thereupon it is possible to display the body from any desirable perspective and to simultaneously insert data from the tomography. The optical representation is calculated from the model.

Such a method is very costly, because a large amount of memory is required as well as considerable processing power. Furthermore, a display in real time is not possible.

From the AT-B 384 544 a method for determining the position of parts of the body is known. According to this specification the respective position is determined by means of ultrasonic sensors in order to determine the mobility of joints. It concerns, however, a purely mathematical method which does not allow graphical representation.

The same disadvantage applies to apparatus described in the DE-C 34 06 179.

The U.S. Pat. No. 4,197,855 describes an apparatus for measuring the movement of the human lower jaw, in which an angular permanent magnet is used to determine the 3D - position. This specification, too, does not provide any processing for graphical representation.

From the DE-A 38 07 578 it is known to measure individual points on the human head by means of video cameras. Together with reference points attached to the head the points to be measured are recorded and electronically collected in a static picture. The optical representation is not even intended for static single images. This provides even less the representation in real time.

BRIEF SUMMARY AND OBJECTS OF THE INVENTION

In view of the foregoing, it is a primary object of the present invention to avoid these disadvantages and to provide a method which allows the combination and the representation of optical displays in a simple, clear and distinct manner.

Consistent with the foregoing objects, and in accordance with the invention as embodied and broadly described herein, a method is disclosed in one embodiment of the present invention which provides that an optical display of the body and a data field allocated to the body are represented simultaneously or alternately from the same perspective and on the same scale in real time. This means that the body can move freely in the recording area. At the same time, this body is displayed in real time, i.e. simultaneously, on a display means. A stored data field is dragged along with the movement of the body and can also be displayed. In this way a high amount of visibility is achieved.

BRIEF DESCRIPTION OF THE DRAWINGS

The foregoing and other objects and features of the present invention will become more fully apparent from the following description and appended claims, taken in conjunction with the accompanying drawing. Understanding that the drawing depicts only a typical embodiment of the invention and is, therefore, not to be considered limiting of its scope, the invention will be described with additional specificity and detail through use of the accompanying drawing in which:

DETAILED DESCRIPTION OF THE PREFERRED EMBODIMENT

Figure 1:
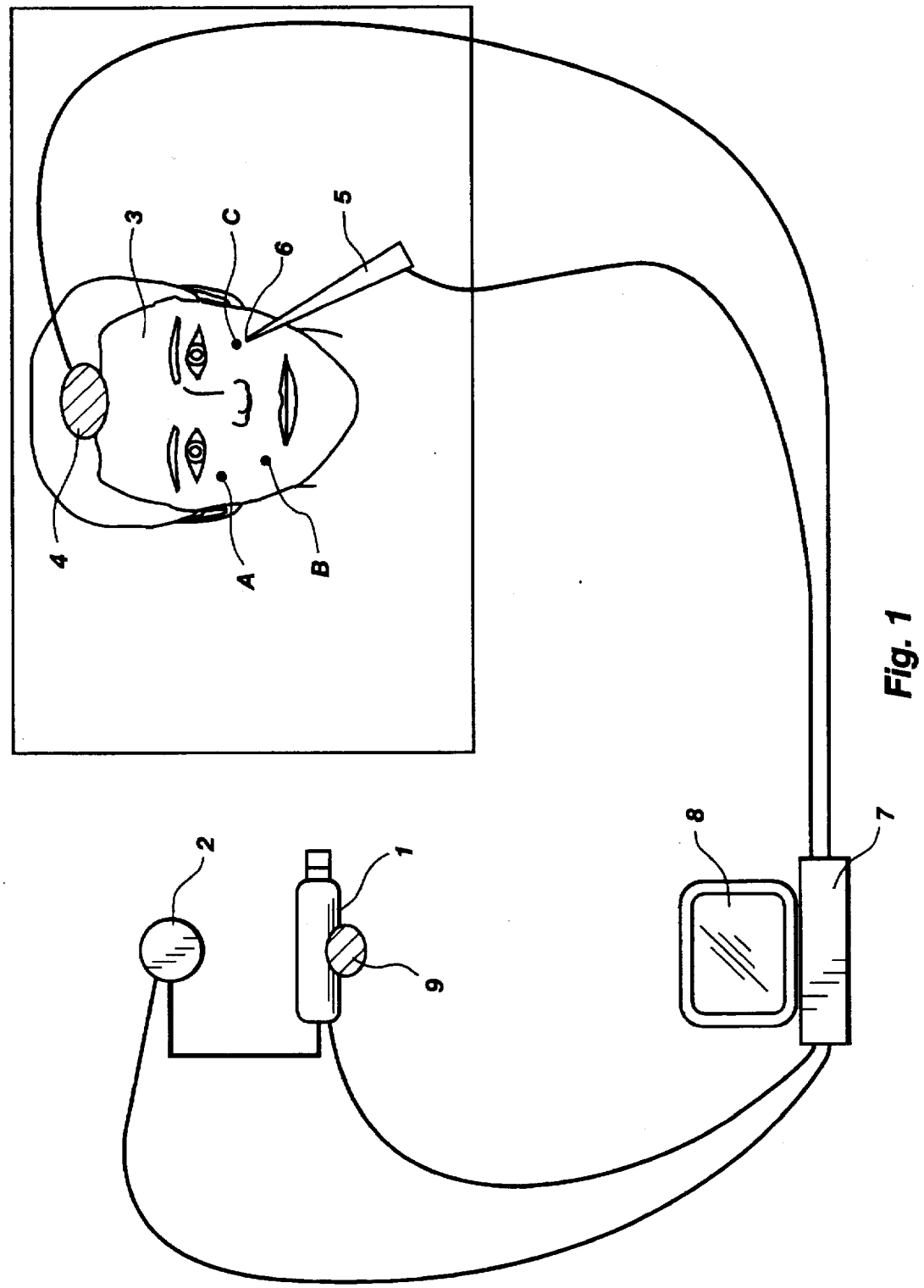
FIG. 1 is a schematic representation of one presently preferred embodiment of the apparatus used in performing the method of the present invention.

It will be readily understood that the components of the present invention, as generally described and illustrated in the Figure herein, could be arranged and designed in a wide variety of different configurations. Thus, the following more detailed description of the embodiment of the system and method of the present invention, as represented in FIG. 1, is not intended to limit the scope of the invention, as claimed, but it is merely representative of the presently preferred embodiment of the invention.

The presently preferred embodiment of the invention will be best understood by reference to the drawing, wherein like parts are designated by like numerals throughout.

The method in accordance with the invention is preferably carried out in accordance with the following steps:

providing an optical image-reproduction system consisting of a camera and a monitor;

allocating a 3D - data field to the body having a certain position;

continuously recording the 3D - position of the body;

continuously calculating a display of the data field equivalent to the body's momentary position; and simultaneously or alternately representing the optical image and the data field on the monitor.

Generally the invention may be used for the representation of any body. However if the body is a human or animal body there are some further preferred embodiments of the method.

It is possible that the position of anatomically characteristic points, an X-ray tomography, a nuclear spin tomography, an ultrasonic image or the like are used as data field. The positions of anatomically characteristic points can, for example, be recorded by means of a 3-D digitizer stylus, i.e. a magnetic stylus. Thus the respective point is marked by the tip of the stylus and, simultaneously, the determination of the precise position is initiated by pressing the enter key. It is clear that this only allows marking points on the surface of the body.

If points in the inside of the body, for example characteristic points of bones, are to be used as data points, the points can be determined by means of sterophotometric measurement on X-rays. A typical case is the measurement of the movement of joints. At first two or more X-rays of the respective limbs are made with the sensors applied to the surface of the skin. Preferably the image planes of these images are orthogonal to one another. This allows determining the coordinates of characteristic points.

In a preferred embodiment of the method it is provided that, for determining the position of the body, a 3-D sensor, preferably a magnetic sensor, is fixedly attached to the body. The continuous determination of the body's position is thus possible in a very simple manner.

The data field, however, need not necessarily be limited to the position of the points of the body itself. An X-ray may be used as data field whose position with respect to the body is determined in such a way that during the X-ray a 3-D sensor is fixedly attached to the body and a further such sensor is attached to the X-ray cassette. The usually two-dimensional X-ray is allocated to a plane outside of the body, e.g. the plane in which the X-ray film was located while the X-ray was made. This X-ray film then constitutes the data field and it is possible to display the body of a patient with this X-ray in such a way as if the X-ray were fixedly attached to said patient.

An ultrasonic display can also be used as a data field in an analogous manner, whereby the position of this display with respect to the body is determined in such a way that during the acoustic irradiation a 3-D sensor, preferably a magnetic sensor, is rigidly attached to the body and a further such sensor is attached to the ultrasonic head.

In a preferred embodiment of the invention it is provided that for recording the position of a body a 3-D sensor, preferably a magnetic sensor, is rigidly attached to the body. Such a sensor consists of a small magnet which not only serves to determine its 3D - position, but also its angular position.

It is possible that the optical image is superimposed on the display of the data field on the screen. It is possible to mix this data field into the optical display. It is, however, also possible to switch back and forth between the optical display and the data display. The user is provided with a large number of options to gain a visual display which offers him the optimal basis for the precise measurement of parts of the body.

It is particularly preferable if the optical image and the display of the data field on the screen can be shown in different window. These windows can, as is well known, be moved, superimposed, zoomed or switched off.

In a particularly preferable embodiment of the method in accordance with the invention it is provided that a part of the displayable data field consists of an arbitrarily selectable imagined axis and that this axis can be achieved by the following steps:

representing of the body as a stationary image in at least two positions;

providing the user with the option to draw the image of the axis into the stationary image;

calculating the 3D - position of the axis; and jointly representing the axis with the body shown with real-time moveability.

If, for example, the axis of a femur is to be superimposed on the image of a human femur, the following procedure is used, the position sensor is attached to a segment of the skin that is little affected by the movement of soft parts. Thereupon single pictures are recorded with the video camera and displayed on the screen either simultaneously or subsequently. The position sensor provides the information on the position of the part of the body at the time when the image was recorded. The user can then draw an axis into each of the single images, for example by means of a mouse. For the computer this represents the projection of an axis located in the three-dimensional space onto the image plane. If the axis was displayed in two different ways, e.g. in a front view and a side view, it is thus possible to determine the 3D -position.

In this context it has proved beneficial to display approximately four single pictures next to one another in one window. The user can use each of these images for entering or altering the axis. As soon as the 3D - position of the axis can be determined it is also calculated for the other images and displayed. This allows a precise check of the input.

In the same way it is possible that a part of the displayable data field consists of an arbitrarily selectable coordinate system whose axes are gained in the manner defined above. After the 3D -determination of one axis of an orthogonal coordinate system it is only necessary to enter a further axis in the image in order to define the position.

After the entry of the axis, the program calculates the position of the axis or axes with respect to the position sensor and is thus able to add said axis to all displays of the parts of the body, so that said axis is moved in accordance with the movements of the parts of the body. The superimposed axis or the coordinate system per se is able to display the data field in accordance with the invention or can be displayed in addition to an X-ray tomography or the like.

It is further possible that a part of the displayable data field comprises at least one point on the skin of the body. Then the following steps are performed:

marking at least one point at the skin;

recording the 3D - position of the point; and simultaneously representing the optical image and the data field including the marked point on the monitor.

It is sometimes a problem that the sensor applied to the skin of a person is affected by movements of the skin relative to the body itself. In this case the system is deceived since the movement of the sensor does not coincide with the movement of the body. Therefore it can be useful to mark at first some points on the skin with color and to record their position then. As long as the relative position of the sensor and the marked points does not change the displayed data points coincide on the monitor with the real images of these points. However if there are displacements due to movements of the skin this does not hold any more. The distance is a measure of the possible error in the display of the data field. With advanced image processing systems it could be possible to correct such error automatically.

Furthermore, the invention relates to an apparatus for displaying moveable bodies. In accordance with the invention this apparatus comprises the following:

a camera;

a monitor;

a position sensor which is rigidly attached to the body to be displayed and which allows the determination of the respective position of this body; and means which allow the simultaneous ar alternate representation of the optical image and the data field on the monitor.

This last mentioned means usually concerns a computer that carries out the necessary calculations. The spatial distance between the focus of the camera optics and the starting point of the field used for the position, i.e. approximately the magnetic field generated by the magnetic field emitter, have to be taken into account. In addition, the relative position of the points of the data field with respect to the position sensor are also included in the calculation. It is also possible, however, that instead of a computer a microprocessor carries out the mentioned calculations.

A particularly simple embodiment of the invention which is easy to realize is provided in that the visual display unit of PC is used as a monitor, whereby the camera is connected to the video input and the data field is transmitted to the PC via a further input. Thus the flow of data originating from recording the optical images is fully transmitted past the computer and therefore does not place a burden on its processing capacity. This allows making use of the full processing power for the additional display of the data field.

The invention is now described in greater detail by reference to an embodiment shown in the Figure of the drawing.

A video camera 1 is rigidly attached to a magnetic field emitter 2. This magnetic field emitter essentially comprises a coil connected to an electric circuit which generates a magnetic field. A magnetic sensor 4 is attached to the head 3 of the patient. This magnetic sensor also includes of coils in which current is induced by the field generated by the magnetic field emitter 2. By measuring these currents it is possible to determine the position of the magnetic sensor 4 with a precision of about one millimeter.

Three measuring points A, B and C are marked by the magnetic stylus 5. The magnetic stylus 5 also comprises coils for recognizing the position, like in the magnetic sensor 4. The marking takes place in such a manner that the tip of stylus 6 is brought to the respective point and then a release button is pressed. The computer 7 stores the momentary position of tip 6 as data point. On the monitor 8 of the computer 7 the head is displayed with the data points A, B and C. It would also be possible to display these data points if they were not visible as real points. For example, if they were located on the side of the head concealed from the camera, they could still be displayed. The position of other covered points can also be displayed. The position of a certain tooth can be marked with stylus 5, which can then be localized even if the mouth is closed. If, however, the tooth is located on the lower jaw, it is necessary to also record the position of this lower jaw. This is possible by attaching a further sensor, which is not shown here. If an additional magnetic sensor 9 is attached to camera 1, it is possible to drop the rigid coupling between the camera 1 and the magnetic field emitter 2. The computer 7 takes into account the variable displacement between camera 1 and magnetic field emitter 2.

The present invention may be embodied in other specific forms without departing from its spirit or essential characteristics. The described embodiments are to be considered in all respects only as illustrative, and not restrictive. The scope of the invention is, therefore, indicated by the appended claims, rather than by the foregoing description. All changes which come within the meaning and range of equivalency of the claims are to be embraced within their scope.

What is claimed and desired to be secured by United States Letters Patent is:

1. A method for displaying a moveable body, the method comprising:

marking a plurality of registration points on the body for tracking movements of a first image;

recording a video image of the body as the first image;

recording data corresponding to spatial coordinates of a plurality of points on the body, distributed in three spatial dimensions;

presenting in real time a second image in three dimensions, the second image corresponding to a three-dimensional image of a portion of the body including the plurality of points, the second image being displayed from the same perspective as the first image and scaled to the same scale as the first image to be superimposable on the first image.

2. A method for displaying a moveable body, the method comprising the following steps:

providing an optical image-reproduction system comprising a video camera for recording a first image comprising a three-dimensional, movable, video image of the body, and a monitor for displaying the first image;

marking a plurality of registration points on the body for tracking movements of the first image;

representing a plurality of points on the body, positioned in a first position, by data corresponding to the spatial coordinates of each point of the plurality of points;

continuously recording the position of the body;

continuously calculating a display of the plurality of points corresponding to the moveable body's momentary position;

selectively representing the first image, the first image superimposed on a second image comprising the plurality of points, and the second image on the monitor.

3. A method for displaying a body, the method comprising:

recording a first image of the body in three dimensions, the image selected from a three-dimensional video image and the body itself;

marking a plurality of registration points on the body for tracking movements of the first image;

recording data corresponding to spatial coordinates of a plurality of points on the body;

presenting on a display in real time the first image;

presenting on the display in real time a second image corresponding to the plurality of points, the second image being presented from the same perspective as the first image and scaled to the same scale as the first image, to be superimposable on the first image.

4. The method of claim 3 wherein each registration point of the plurality of registration points corresponds to a point of the plurality of points.

5. The method of claim 4 further comprising registering the first image with the second image by matching corresponding registration points in the first and second images.

6. A method for displaying a body, the method comprising the following steps:

provicing an image-reproduction system comprising a video camera for recording a three-dimensional image of the body displaying simultaneously actual points on the body, the points being viewed from a perspective of the image-reproduction system and a monitor for displaying a first image corresponding to the three-dimensional image of the body;

placing on the body a plurality of marks associated with a plurality of registration points;

representing a plurality of points on the body, positioned in a first position, by data corresponding to spatial coordinates of each point of the plurality of points;

continuously recording and presenting the first image corresponding to the body while the body moves;

continuously calculating and presenting a second image corresponding to the plurality of points on the body while the body moves;

selectively representing on the monitor the first image, the second image, and a combination image superimposing the first and second images.

7. The method of claim 6 wherein each registration point of the plurality of registration points corresponds to a point of the plurality of points.

8. The method of claim 7 wherein said each mark is detectable by the camera.

9. The method of claim 8 further comprising registering the first image with the second image by positioning each mark in the first image over the corresponding registration point in the second image.

10. The method of claim 9 further comprising scaling and orienting the second image to be presented from the same perspective and scaled to the same size as the first image.

11. The method of claim 10 further comprising superimposing the second image on the first image.

12. A method for displaying a body, the method comprising:

providing an optical image-reproduction system comprising a video camera and a corresponding monitor;

placing on the body a plurality of marks associated with a plurality of registration points;

allocating a three-dimensional data field to the body in a first position;

continuously recording with the camera in three spatial dimensions a first image of the body showing the positions of points, including at least one registration point, on the body;

repeatedly calculating the positions of a plurality of points in the three-dimensional data field, corresponding no the positions of the points on the body;

presenting on the monitor, selectively, the first image and a second image corresponding to the plurality of points, and a third image corresponding to the plurality of points superimposed on the first image.

* * * * *